United States Patent [19]
Loeb et al.

[11] Patent Number: 5,466,234
[45] Date of Patent: Nov. 14, 1995

[54] EXPANDABLE LASER CATHETER

[75] Inventors: Marvin P. Loeb, Huntington Beach; Samuel M. Shaolian, Laguna Niguel; Vahid Saadatmanesh, Irvine; Jeffrey J. Giba, Moreno Valley; To V. Pham, Trabuco Canyon, all of Calif.

[73] Assignee: Trimedyne, Inc., Irvine, Calif.

[21] Appl. No.: 189,375

[22] Filed: Jan. 31, 1994

[51] Int. Cl.[6] .................................................. A61B 17/36
[52] U.S. Cl. .................................. 606/15; 606/7; 606/16
[58] Field of Search .................................. 606/7, 13–16; 607/88, 89

[56] References Cited

U.S. PATENT DOCUMENTS

| | | |
|---|---|---|
| 3,498,286 | 3/1970 | Polanyi et al. . |
| 3,866,599 | 2/1975 | Johnson . |
| 4,681,104 | 7/1987 | Edelman . |
| 4,781,681 | 11/1988 | Sharrow et al. . |
| 4,790,310 | 12/1988 | Ginsburg et al. . |
| 5,019,075 | 5/1991 | Spears et al. ............................ 606/7 |
| 5,066,292 | 11/1991 | Müller et al. ............................ 606/7 |
| 5,169,395 | 12/1992 | Narciso, Jr. . |
| 5,176,674 | 1/1993 | Hofmann ................................ 606/7 |
| 5,188,632 | 2/1993 | Goldenberg ............................ 606/7 |
| 5,203,779 | 4/1993 | Müller et al. . |

Primary Examiner—Stephen C. Pellegrino
Assistant Examiner—Michael Peffley
Attorney, Agent, or Firm—Olson & Hierl, Ltd.

[57] ABSTRACT

A catheter suitable for the delivery of laser energy to an obstruction in a body lumen is provided, which has an expandable, elastic distal end portion containing optical fibers whose exposed distal end faces are arranged in two or more substantially concentric arrays that merge into a narrower band array of a larger diameter upon radial expansion of the elastic distal end portion. The distal end portion of the catheter is more elastomeric than the catheter body.

27 Claims, 4 Drawing Sheets

EXPANDABLE LASER CATHETER

FIELD OF THE INVENTION

This invention pertains to catheters for delivery of radiant energy. More particularly, the invention pertains to catheters for delivering directable laser energy to an obstructed region of a corporal lumen such as a blood vessel to ameliorate or remove the obstruction.

BACKGROUND OF THE INVENTION

Lasers have been used to provide heat energy, directly or indirectly, for the purpose of removing plaque or other obstructing materials in a corporal lumen. One such system is disclosed in Ginsburg et al. U.S. Pat. No. 4,790,310 (the '310 patent) entitled "Laser Catheter Having Wide Angle Sweep." Another such system is disclosed in Müiller et al. U.S. Pat. No. 5,066,292 (the '292 patent) entitled "Catheter System For Vessel Recanalization In The Human Body."

In the catheter device of the '310 patent, laser energy is output from a distal end via four directable optical fibers. The optical fibers are evenly spaced from one another about the lumen of the catheter. A segmented distal end portion of the catheter spreads apart to enlarge the optical fiber spacing. The expanded spacing of optical fibers redirects the path of the emitted laser energy.

In the catheter device of the '292 patent, laser energy is also output from a distal end via directable optical fibers. The optical fibers are arranged in jointed groups. Upon expansion of the catheter a distal end portion of the ring of optical fibers is expanded only in selected regions between jointed groups.

Although the devices disclosed in the above patents provide directable laser energy, several disadvantages exist. As the distal end portion of each device expands, the laser energy per area (power density) necessarily decreases since each optical fiber or optical fiber group moves apart from adjacent optical fibers. This causes the power density to decrease at a rate inversely proportional to the expansion of the distal end portion. Decreased power density will increase the time and possibly reduce the effectiveness of the procedure to remove the corporal lumen obstruction.

There continues to be a need to provide a cost effective catheter for efficient delivery of directable radiant energy, such as laser, for ablation of obstructions in a corporal lumen.

SUMMARY OF THE INVENTION

A catheter device for controllable delivery of radiant energy to a selected region within a corporal lumen includes optical fibers for delivery of energy from an expandable elastomeric distal end. The expandable elastomeric distal end has a greater elasticity than the rest of the catheter. The optical fibers preferably are arranged at the distal end of the catheter into at least two generally adjacent, substantially concentric annular arrays or in a generally annular compartmental arrangement. The optical fibers can be situated along and substantially parallel thereto the axis of the catheter. Or, the optical fibers may form a helix about the longitudinal axis of the catheter as long as they conduct radiant energy to the distal end of the catheter. The individual optical fibers can be tapered to alter the cross-section toward the distal end to distribute the laser energy over a larger area, if desired. The optical fibers may also have varying diameters.

At their distal end portion, the optical fibers can be bundled together by an elastic casing or a conventional binder, such as an elastic potting material. The elastic potting material can fill the spaces between the optical fibers at the distal end portion.

Alternatively, the potting material can be used from about 4 cm to 20 cm from the distal end face to secure the optical fibers along the catheter. This arrangement is used when no potting material is used at the distal end portion of the catheter or when the potting material used at the distal end portion is too soft to allow polishing of the catheter without the inner potting of the optical fibers.

The catheter terminates in a distal end portion which is made of an elastomeric material that facilitates the expansion of the distal end together with the optical fibers. The distal end is expanded by an expansion device preferably from within the distal end portion of the catheter. This device is preferably of an inflatable nature, such as a balloon. Alternatively, the distal end can be expanded by applying a tapered device, such as a wedge, a camming surface of which can be urged into the distal end to achieve the desired expansion.

The expansion device is manipulated via a channel which is situated generally central in the catheter. The channel may be centered axially in the catheter. The channel may also define a conduit for a guidewire. The channel may terminate at the distal end, or in, adjacent, or proximal to the distal end portion.

When the expansion device is actuated, the distal end portion expands radially. As the distal end portion expands, the substantially concentric annular arrays of optical fibers are urged closer to one another and merge at least in part into a single annular array. Optical fibers from one array are urged into the spaces between optical fibers of an adjacent array. In effect, this expanded arrangement provides radiant energy delivery substantially uniformly about the circumference of that array. Thus, a predetermined density can be substantially maintained as the distal end of the catheter is expanded.

Other embodiments of the present invention include optical fibers having different diameters or cross-sectional geometries to facilitate this expanded arrangement. Moreover, a catheter having an exterior cross-sectional geometry that facilitates the merger of optical fiber-arrays upon expansion can also be utilized. For example, the body of the catheter may be axially fluted. Such a structure facilitates the merger of the optical fibers present since the fluted regions of the distal end portion deform more than the nonfluted regions.

A radiopaque marker can be situated at or near the distal end portion of the present laser catheter device so that the position of this device in a corporal lumen can be ascertained radiographically.

A preferred procedure to ablate an obstruction in a body corporal lumen, such as a blood vessel, using a catheter embodying the present invention includes the use of a guidewire the distal end of which is extended into or beyond the obstruction. Next, the laser catheter is inserted into the corporal lumen over the guidewire and advanced up to the obstruction. An expansion device, such as a balloon, is then expanded to a desired dimension to increase the diameter of a distal end portion of the catheter. Thereafter, laser energy is emitted from the distal end portion of the catheter to ablate the obstruction while the distal end portion of the catheter is urged forwardly. The expansion device, such as a balloon, may be disposed within the catheter beneath the elastomeric potting material encasing the distal ends of the optical fibers, or it may be mounted on the guidewire.

This procedure may also entail, after the distal end of the laser catheter has first passed through the obstruction, expanding the distal end of the catheter by the expansion means to further increase its diameter, activating the laser and pulling the catheter back through the obstruction in a retrograde manner, or withdrawing the catheter from the obstruction, expanding the distal end portion by the expansion means to further increase its diameter, and then again emitting laser energy, creating a relatively larger channel through the obstruction.

Another procedure can be performed where the expansion device alternatively expands and contracts the distal end portion of the catheter while laser energy is being emitted, and the distal end portion is urged through the obstruction.

Once the obstruction is minimized or removed, the catheter can be repositioned in the corporal lumen to the site of another obstruction, and the above procedures can be repeated.

Numerous other advantages and features of the present invention will become readily apparent from the following detailed description of the invention and the embodiments thereof, from the claims and from the accompanying drawings in which details of the invention are fully and completely disclosed as a part of this specification.

DETAILED DESCRIPTION OF THE PREFERRED EMBODIMENTS

Figure 1:
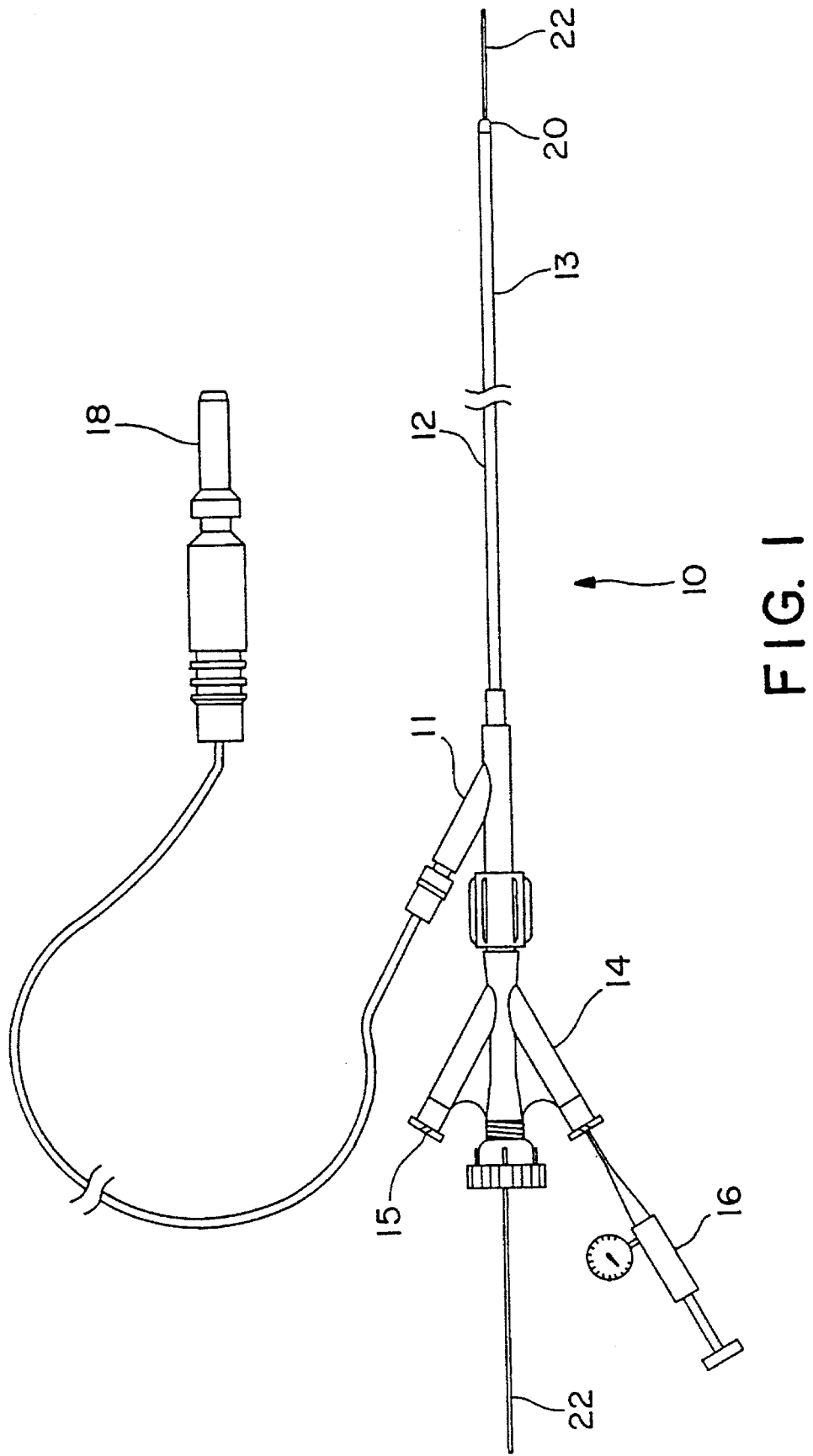
FIG. 1 is an overall, partially fragmented view of a laser catheter embodying the present invention.

While this invention is susceptible of embodiment in many different forms, there are shown in the drawings and will be described herein in detail specific embodiments thereof with the understanding that the present disclosure is to be considered as an exemplification of the principles of the invention and is not to be limited to the specific embodiments illustrated.

As shown in FIG. 1, one preferred embodiment of a laser catheter assembly 10 according to the present invention includes a catheter 12, preferably associated with a conventional hemostatic "Y" connector 14 and hemostatic "Y" optical fiber port 11, through which optical fibers (not shown) extend into laser connector 18, as known in the art. Hemostatic "Y" connector 14 is connected to a syringe or inflation apparatus 16, as known in the art, and communicates with an inflation duct and a balloon (not shown) in catheter 12. Catheter 12 has a body portion 13 that terminates in a distal elastomeric end portion 20. Hemostatic "Y" fluid port 15 communicates with a central channel (not shown) in catheter 12, which channel extends through catheter body 13 and distal elastomeric end portion 20 for infusion of radio-opaque and other fluids. Extending through said central channel of catheter 12 is a conventional guidewire 22.

Figure 2:
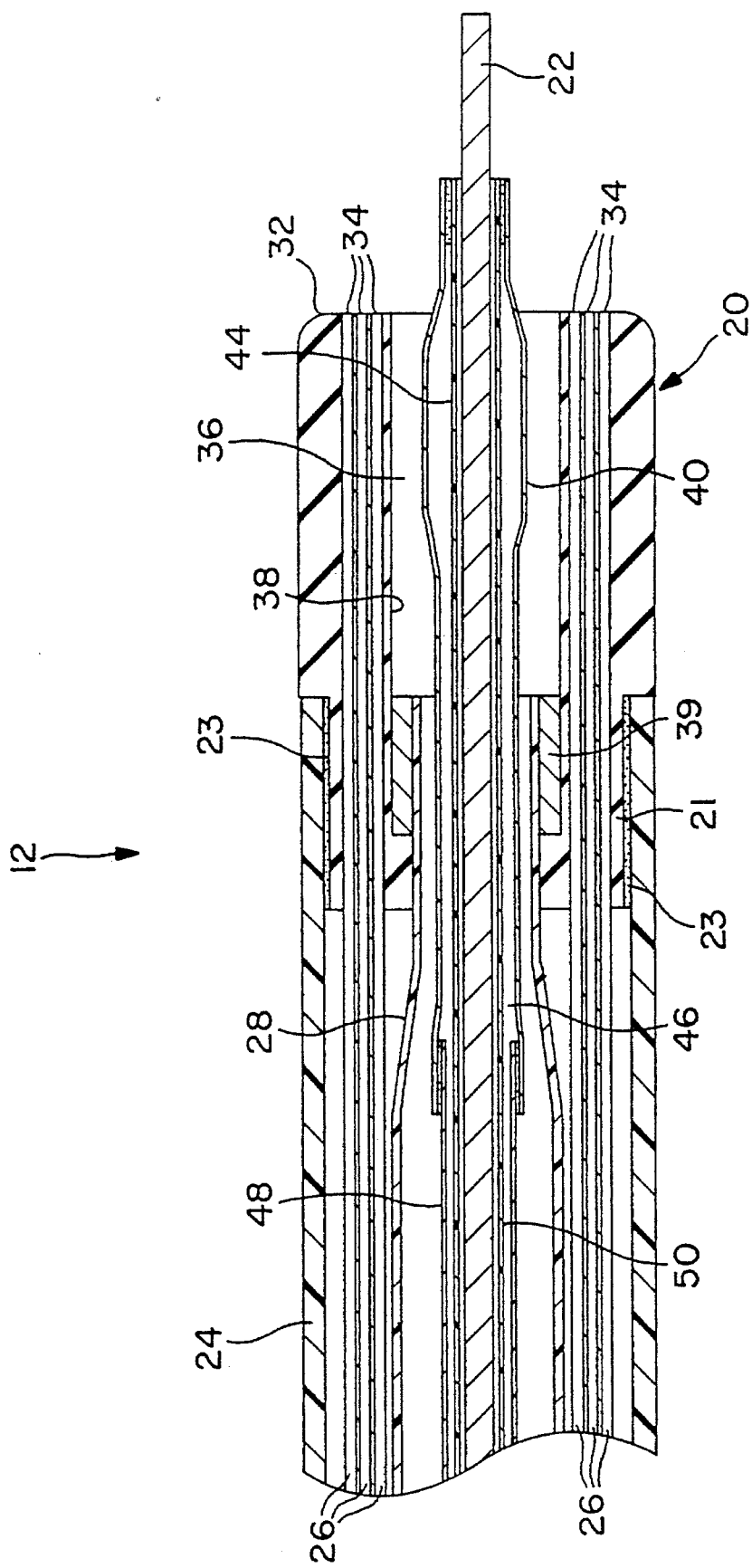
FIG. 2 is an enlarged sectional view of the catheter distal end portion of the catheter shown in FIG. 1.

Referring to FIG. 2, the exterior of catheter 12 is defined by outer tube 24 which abuts distal end portion 20. Elastomeric skirt 21 is unitary with distal elastomeric end portion 20 and is attached to outer tube 24 by adhesive layer 23. Optical fibers 26 are situated along the longitudinal axis of the catheter and substantially parallel thereto. The sizes of individual optical fibers can vary. Also, the catheter distal end portion can include optical fibers of different diameters, some or all of which may be tapered to produce a larger end face area at their distal ends. Presently preferred are optical fibers having a core diameter of about 50 µm, but can range from about 30 µm to 300 µm. Hollow inner tube 44 is generally centrally located in catheter 12, defines a central channel 50 therethrough and may terminate at the distal end of distal elastomeric end portion 20 or may extend about 2 to 15 mm distally therefrom. Guidewire 22 slidably extends through the central channel 50 of inner tube 44. Middle hollow tube 28 may optionally be included to hold optical fibers 34 in place, extending through the central body of catheter 12 and terminating proximal to the main body of distal elastomeric end portion 20.

Distal elastomeric end portion 20 is made of an elastomeric material, such as polyurethane, having a Shore Durometer hardness value of about 70A. The elastomeric material holds the fibers in place for polishing their end faces, and it prevents broken fibers from exiting the laser catheter and their having to be removed from an artery surgically. Preferably the length-to-diameter ratio for the distal elastomeric end portion 20 is about 0.8 to about 1.2 for coronary artery use and about 1.5 to 0.8 for peripheral artery use. The external diameter of the distal end portion is substantially the same as that of catheter 12, itself, and can range from about 1.0 mm to about 6.0 mm.

In a typical laser catheter embodying the present invention for coronary artery use, the external diameter of the elastomeric distal end portion 20 in a non-expanded state is about 1.3 to 2.2 mm and the length of distal elastomeric end portion 20 extending distally from the distal end of outer tube 24 is about 1.5 to 4.0 mm.

For peripheral artery use, the external diameter of distal elastomeric end portion 20 in an unexpanded state is about 2.5 mm to 6.0 mm and the length of same extending from the distal end of catheter 12 is about 2.0 mm to 8.0 mm.

The composition of optical fibers 26 is dependent upon the type of laser energy that is to be transmitted through the fibers. Contemplated laser wavelengths for the present purposes are those of an excimer laser (wavelengths of 0.308 microns or 0.349 microns), requiring high OH quartz optical fibers; pulsed or continuous Nd:YAG lasers (wavelengths of 0.355 microns, 0.532 microns, 1.064 microns or 1,432 microns), enabling conventional quartz or fused silica optical fibers to be used; pulsed holmium:YAG lasers (wavelength of 2.01 microns), requiring low OH quartz optical fibers; and the like.

Catheter body portion 13 is composed, itself, of two portions. The distal 13–22 cm thereof has a shore hardness value of 100A, providing greater flexibility to the distal portion of catheter body portion 13. The proximal 100–120 cm portion of catheter body 13 has a shore hardness value of 60–70 D, providing greater pushability for that portion of body portion 13. These two segments are fused or bound together by a thermal welding process or an adhesive, as known in the art.

The distal ends of optical fibers 26 preferably are embedded in distal elastomeric end portion 20 and terminate at exposed end faces 34 that are substantially even with catheter distal end face 32.

A radiopaque material 39, such as platinum or gold foil, preferably is positioned proximal to the main body of distal elastomeric end portion 20, and may be attached to elastomeric skirt 21 thereof or to middle hollow tube 28, to enable monitoring of the location of the catheter tip within a body lumen radiographically.

An expansion chamber 36 is defined by the interior surface 38 of distal elastomeric end portion 20 and an expansion device, balloon 40, surrounding inner hollow tube 44. Balloon 40 is inflated through inflation duct 46 of balloon 40. Inflation duct 46 is in fluid communication with hemostatic "Y" connector 14 (not shown).

Inner tube 44 defines a central channel 50 for slidably receiving guidewire 22 which, as shown in FIG. 2, extends through central channel 50 and beyond the distal end face 32 of catheter 12. Hemostatic fluid port 15 (not shown) is in fluid communication with central channel 50 for infusion of radiopaque fluids, saline or drugs. Balloon 40 may be contiguous with balloon tube 48, or balloon 40 may be joined to balloon tube 48 by thermal welding and an adhesive, as known in the art. Balloon 40 and balloon tube 48 can be made of polyurethane tubing, or balloon tube 48 can be made of a less elastic grade of polyurethane tubing, a heat shrinkable plastic tubing or the like.

Figure 3:
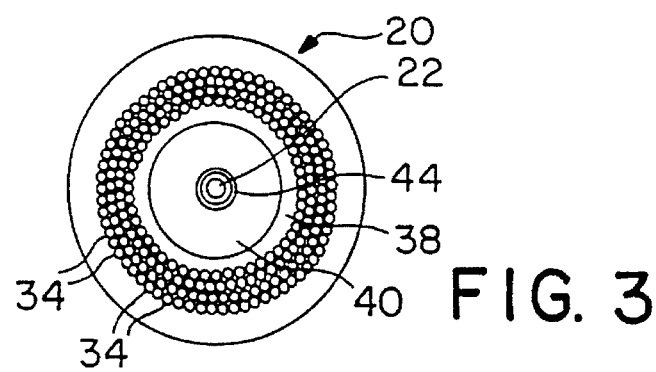
FIG. 3 is an end view of the catheter shown in FIG. 2.

A preferred arrangement of exposed end faces 34 of optical fibers 26 can best be seen by reference to FIG. 3. Shown are four rows of optical fibers with respective end faces 34 arranged as generally adjacent, substantially concentric annular arrays embedded in distal elastic end portion 20.

Figure 4:
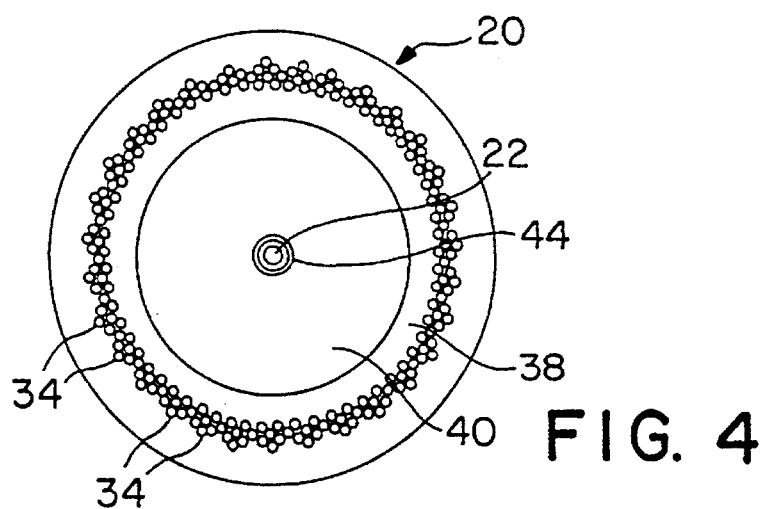
FIG. 4 is a sectional view similar to that of FIG. 3 but in an expanded condition.

The operation of the present preferred embodiment may be illustrated by referring to FIG. 4 in conjunction with FIG. 2. Balloon 40 is pressurized via inflation duct 46 and expands in cavity 36 against inner surface 38 of distal elastomeric end portion 20. As the diameter of distal elastomeric end portion 20 increases, the separate annular arrays of optical fibers 26 merge into a substantially narrower array of a substantially increased diameter. Optical fibers 26 in an outer annular array are repositioned during expansion of balloon 40 farther from one another forming a space therebetween. The formed space is then taken up, at least in part, by some of the optical fibers in the next inner array.

As shown in FIG. 4, as the respective individual annular arrays commingle, a single, substantially continuous annular array is maintained. Thus, laser energy from optical fibers 26 does not undergo a substantial loss in its energy density over the expanded annular arrays.

Figure 5:
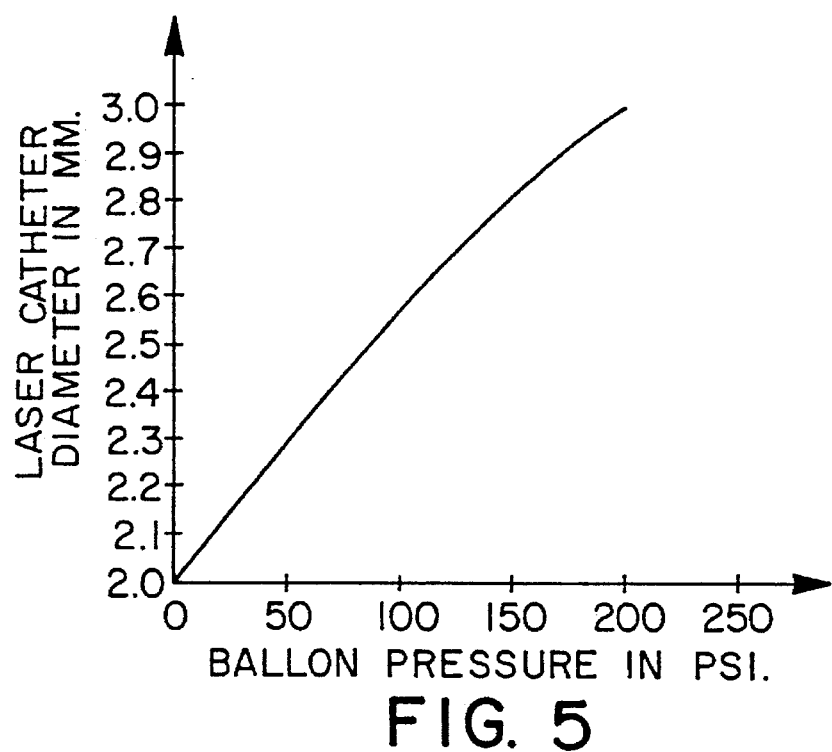
FIG. 5 is a graphical illustration of the catheter diameter as a function of applied pressure.

FIG. 5 shows the relationship between the diameter of distal elastic end portion of a catheter embodying this invention and the pressure applied to its expansion balloon. As can be seen, the diameter of distal elastomeric end portion is a generally linear function of the pressure applied to the balloon.

Optionally, the optical fibers 26 may be disposed in two or more bundles at their proximal ends and arranged in a similar number of sections in an annular array at their distal ends, so that the laser energy may be transmitted serially thereinto, from one bundle to the other, and emitted therefrom from one section to the next, or in such other pattern as may be desired.

Figure 6:
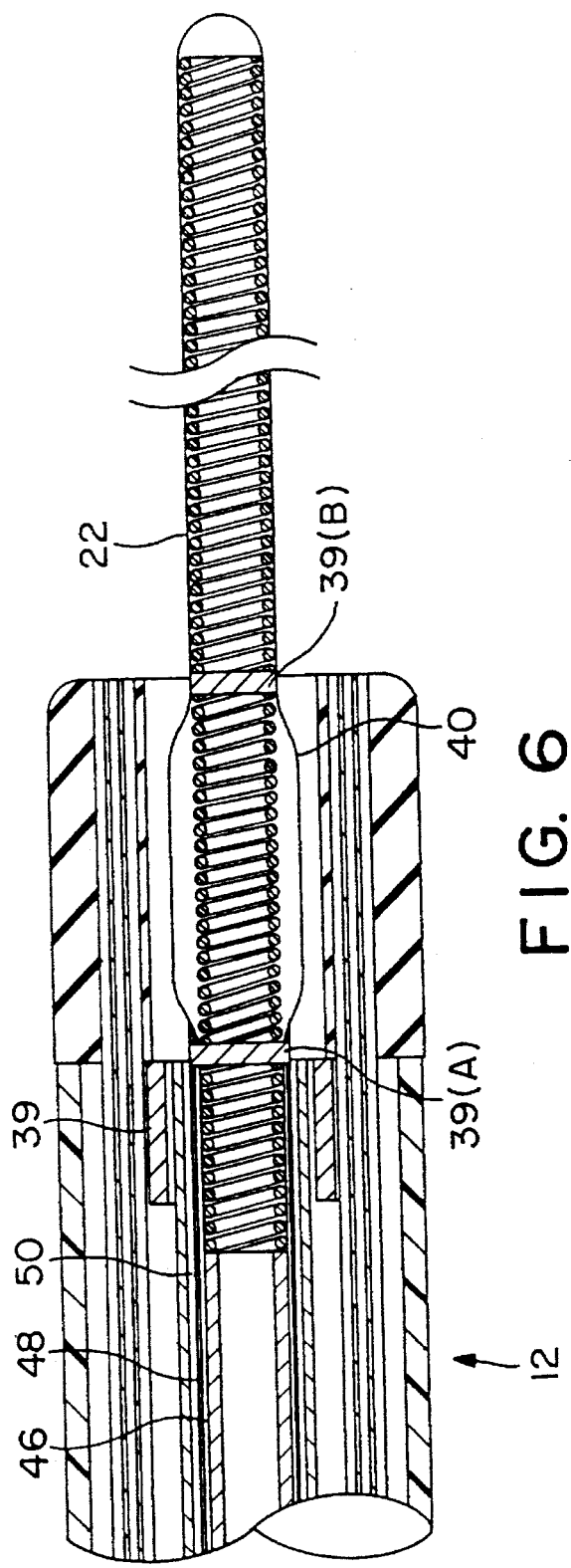
FIG. 6 is a cross-sectional view of an alternate embodiment of the expanding means of the present invention.

In a alternative embodiment, as seen in FIG. 6, balloon tube 48 extends over guidewire 22 and terminates at balloon 40, which is disposed about guidewire 22 near its distal end. Guidewire 22 slidably extends through central channel 50 of laser catheter 12. Radiopaque markers 39(A) and 39(B) are disposed about the proximal and distal ends of balloon 40 to enable its position relative to radiopaque marker 39 of laser catheter 12 to be ascertained radiographically. Balloon 40 is inflated by inflation channel 46, which is created by the space between balloon tube 46 and guidewire 22.

Figure 7:
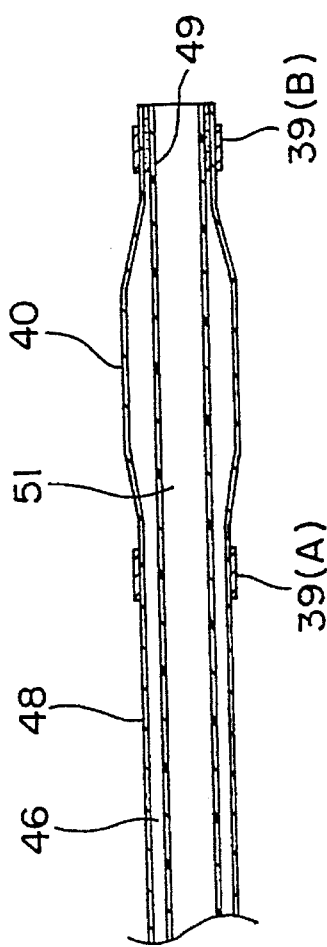
FIG. 7 is a cross-sectional view of an alternative embodiment of the expanding means of the present invention.

As seen in FIG. 7, in this embodiment, balloon tube 48 is disposed about independent flexible tube 49 and terminates at balloon 40, which is disposed about the distal end of independent flexible tube 49, creating inflation channel 46 therebetween. Radiopaque markers 39(A) and 39(B) enable the location of the balloon 40 to be ascertained radiographically. This assemblage is slidably moveable through central channel 50 of laser catheter 12 (not shown). Guidewire 22 (not shown) is slidably moveable through central channel 51 of independent flexible tube 49.

Components such as lasers, laser connectors, optical fibers, guidewires, "Y" connectors, syringes and inflation devices, all as known in the art, are not described in detail herein and form no part of the present invention. Numerous variations and modifications of the embodiments described above may be effected without departing from the spirit and scope of the novel features of the invention. It is to be understood that no limitations with respect to the specific device illustrated herein are intended or should be inferred. It is, of course, intended to cover by the appended claims all such modifications as fall within the scope of the claims.

We claim:

1. A laser catheter having a proximal end for connection to a laser source, a body portion, and an elastic distal end portion, which catheter comprises:

(a) a plurality of optical fibers having exposed optical fiber end faces situated in the elastic distal end portion and arranged in at least two substantially concentric annular arrays;

(b) a hollow, flexible shaft centrally situated within the catheter and defining a central channel therethrough; and (c) an inflatable means for expanding the elastic distal end portion of the laser catheter to increase the spaces between the optical fibers in said annular arrays and force at least some of the underlying optical fibers into the spaces created thereby.

2. The catheter of claim 1 wherein the elastic distal end portion of the catheter is more elastomeric than the catheter body portion.

3. The catheter of claim 1 further comprising a radiopaque marker associated with the distal end portion thereof.

4. The catheter of claim 1 wherein a guidewire may slidably extend through the central channel thereof.

5. The catheter of claim 1 wherein the elastic distal end portion defines a cavity coaxial therewith, and wherein the inflatable means is situated within the cavity.

6. The catheter of claim 5 wherein the inflatable means is a balloon.

7. The catheter of claim 1 wherein the inflatable means is a balloon mounted near the distal end of a guidewire slidably disposed within the central channel of the laser catheter.

8. The catheter of claim 1 wherein the inflatable means is a balloon at the distal end of an independent member slidably disposed in the central channel of the laser catheter.

9. The catheter of claim 1 wherein the optical fibers are embedded in the elastic distal end portion of the laser catheter.

10. A laser catheter having a proximal end, a body portion and a hollow expandable, elastomeric distal end portion including a distal end face, which catheter comprises:
(a) optical fibers extending from the proximal end of the catheter and adapted for operable association with a laser source at the proximal end, said optical fibers being embedded in the elastomeric distal end portion, terminating in a plurality of exposed end faces coplanar with the distal end face of the catheter and arranged in at least two substantially concentric annular arrays;
(b) a hollow flexible shaft centrally situated within the catheter and defining a central channel along the longitudinal axis of the catheter; and
(c) an expandable member mounted near the distal end of a guidewire for independent axial movement through said central channel which, upon expansion within the elastomeric distal end portion, causes said annular arrays of optical fibers to merge at least in part into an annular array of a greater diameter.

11. A laser catheter having a proximal end connectable to a laser source, a body portion, the exterior of which is defined by an outer tube, and an expandable, hollow distal end portion, which catheter comprises:
(a) optical fibers disposed in at least two annular arrays, adaptable to the laser source and terminating at the distal end of the expandable, hollow distal end portion in substantially concentric annular arrays;
(b) a hollow flexible shaft situated within the catheter and defining a central channel, the optical fibers being disposed between the outer tube of the body portion and the hollow, flexible shaft; and
(c) a balloon situated in a cavity within the expandable, hollow distal end portion beneath the optical fibers.

12. The laser catheter of claim 11, in which an elastomeric potting material is disposed about the distal ends of the optical fibers.

13. The laser catheter of claim 11 in which an elastomeric potting material is disposed about the optical fibers 4 to 20 cm proximal to the distal ends of the optical fibers.

14. A laser catheter having a proximal end for connection to a laser source, a catheter body, and an expandable elastic distal end portion that is more elastomeric than the catheter body, which catheter comprises:
(a) a plurality of optical fibers extending through the laser catheter and terminating in a generally annular array co-planar with the elastic distal end portion of the catheter;
(b) a hollow flexible shaft centrally situated within the catheter and defining a central channel therethrough; and
(c) a means for expanding the elastic distal end portion of the catheter associated with the central channel to cause the annular array of optical fibers to increase in diameter,
wherein the optical fibers are disposed in two or more concentric rings which, upon expansion of the elastic distal end portion, merge into an annular array of a greater diameter.

15. The catheter in accordance with claim 14 wherein the optical fibers have a core diameter in the range of about 30 microns to about 300 microns.

16. The catheter in accordance with claim 14 wherein the optical fibers are disposed in bundles at their proximal ends and in an annular segmented arrangement at their distal ends.

17. The catheter in accordance with claim 14 wherein an elastic potting material binds the optical fibers together at the distal end portion of the laser catheter.

18. The catheter in accordance with claim 14 wherein the means for expanding the distal end portion of the catheter is a balloon disposed within the distal end portion of a catheter, beneath the elastic potting material.

19. The catheter in accordance with claim 14 wherein the means for expanding the distal end portion of the catheter is a balloon mounted near the distal end of a guidewire and movably disposed in the hollow flexible shaft of the laser catheter.

20. The catheter in accordance with claim 14 wherein the means for expanding the distal end portion of the catheter is a balloon mounted on an independent hollow member movably disposed in the hollow flexible shaft of the laser catheter, through which independent hollow member a guidewire may be slidably received.

21. A laser catheter having a proximal end for operable association with a laser source and an expandable elastic distal end portion, which catheter comprises:
(a) a plurality of optical fibers extending from the proximal end of the catheter through the catheter and terminating in a substantially annular array of end faces at the distal end of the expandable elastic distal end portion of the catheter, the annular array having a thickness greater than a diameter of one of the optical fibers;
(b) an elastic potting material retaining the optical fibers at the distal end portion of the catheter in a predetermined alignment;
(c) a flexible tube, defining a central channel in at least the distal end portion of the catheter; and
(d) a means for expanding the elastic distal end portion of the catheter associated with the tube to enlarge the diameter of the annular array of optical fibers.

22. The laser catheter of claim 21 in which the optical fibers are arranged in at least two concentric rings which, when the elastic distal end portion of the catheter is expanded, expand into a thinner ring of a greater diameter.

23. A procedure for ablating an obstruction in a blood vessel or body lumen utilizing a catheter with an expandable, elastic distal end portion, a plurality of optical fibers arranged in an annular array at the distal end face of the elastic distal end portion, a balloon disposed beneath the elastic distal end portion of the catheter and a central channel through the catheter, comprising the steps of:
(a) introducing a guide wire into the obstructed blood vessel or lumen and extending the distal end portion of the guidewire through the obstruction;
(b) inserting the catheter into the blood vessel or lumen over the guidewire and advancing the inserted catheter to the obstruction;
(c) expanding the balloon so as to increase the diameter of the distal end portion of the catheter to a desired dimension while providing radiant energy deliverable substantially uniformly about the circumference of the annular array; and
(d) emitting laser energy from the distal end face of the catheter while urging the distal end portion of the catheter through the obstruction,
wherein the distal end faces of the optical fibers are arranged in two or more concentric rings so that, when the elastic distal end portion of the catheter is expanded, the optical fibers in the inner rings are forced at least partially into the spaces between the next outer ring of optical fibers.

24. The procedure in accordance with claim 23 wherein the catheter, after its elastic distal end portion has once passed through the obstruction, is withdrawn from the obstruction, the balloon is expanded to a relatively larger dimension, further increasing the diameter of the distal end face of the catheter, and then emitting laser energy as the distal end portion of the catheter is urged through the obstruction, thereby ablating a relatively larger channel through the obstruction.

25. The procedure in accordance with claim 23, wherein the catheter, after its elastic distal end portion has once passed through the obstruction, the balloon is expanded to increased the diameter of the distal end face of the catheter and, as laser energy is emitted from the distal end faces of the optical fibers, the catheter is pulled back through the obstruction in a retrograde manner, thereby ablating a relatively larger channel through the obstruction.

26. The procedure in accordance with claim 23, wherein the balloon is successively inflated and deflated while laser energy is being emitted from the distal end face of the catheter and while the distal end portion of the catheter is urged through the obstruction.

27. The procedure in accordance with claim 23, wherein the catheter is positioned in the blood vessel or body lumen at the site of another obstruction and steps (a) through (d) are repeated.

* * * * *